United States Patent
Niekawa et al.

(10) Patent No.: US 8,399,846 B2
(45) Date of Patent: Mar. 19, 2013

(54) RADIATION IMAGE DETECTING SYSTEM

(75) Inventors: Yukihiro Niekawa, Hachioji (JP); Yoshihiko Eguchi, Tokorozawa (JP)

(73) Assignee: Konica Minolta Medical & Graphic, Inc. (JP)

( * ) Notice: Subject to any disclaimer, the term of this patent is extended or adjusted under 35 U.S.C. 154(b) by 9 days.

(21) Appl. No.: 13/255,929

(22) PCT Filed: Feb. 18, 2010

(86) PCT No.: PCT/JP2010/052400
§ 371 (c)(1),
(2), (4) Date: Sep. 12, 2011

(87) PCT Pub. No.: WO2010/109984
PCT Pub. Date: Sep. 30, 2010

(65) Prior Publication Data
US 2012/0006994 A1    Jan. 12, 2012

(30) Foreign Application Priority Data
Mar. 24, 2009    (JP) .................................. 2009-071405

(51) Int. Cl.
*G01T 1/24* (2006.01)
*H01J 7/00* (2006.01)

(52) U.S. Cl. .................................. 250/370.08; 320/138

(58) Field of Classification Search ............. 250/370.08, 250/370.09, 371; 320/137, 138, 165
See application file for complete search history.

(56) References Cited

U.S. PATENT DOCUMENTS
2007/0140424 A1  6/2007 Serceki
2009/0026378 A1  1/2009 Yoshimi et al.
2009/0195209 A1*  8/2009 Nishino et al. ................ 320/134

FOREIGN PATENT DOCUMENTS
| JP | 6-342099 A | 12/1994 |
| JP | 7246199 A | 9/1995 |
| JP | 2001-224579 A | 8/2001 |
| JP | 3302163 B2 | 4/2002 |
| JP | 2007-167649 A | 7/2007 |
| JP | 2008-43038 A | 2/2008 |
| JP | 2009-53670 A | 3/2009 |

OTHER PUBLICATIONS

International Search Report for International Application No. PCT/JP2010/052400 mailed May 18, 2010 with English translation.
Katsuhiko Naoi, "Recent advances in electrochemical supercapacitors", Kagaku Kogyo, Oct. 1, 2008, Vo. 59, No. 10, pp. 770-775, Okuzuke (English translation not available).

* cited by examiner

*Primary Examiner* — Mark R Gaworecki
(74) *Attorney, Agent, or Firm* — Cantor Colburn LLP

(57) ABSTRACT

Provided is a radiation image detecting system including a cassette type radiation image detecting apparatus capable of being driven by electric power supplied from a built-in battery; a charge controlling circuit to control charging of the battery; a cradle supplying electric power to the radiation image detecting apparatus; and a cable supplying electric power to the radiation image detecting apparatus, wherein the radiation image detecting apparatus includes a connection section being electrically connected to each of the cradle and the cable to receive the electric power; the battery is charged by the cradle being connected to the connection section and by the cable being connected to the connection section; and the charge controlling circuit switches a charging current between a time when the cradle is connected to the connection section and a time when the cable is connected to the connection section.

5 Claims, 11 Drawing Sheets

RADIATION IMAGE DETECTING SYSTEM

CROSS REFERENCE TO RELATED APPLICATIONS

This is a U.S. national stage of application No. PCT/JP2010/052400, filed on Feb. 18, 2010. Priority under 35 U.S.C. §119(a) and 35 U.S.C. §365(b) is claimed from Japanese Application No. JP2009-071405, filed Mar. 24, 2009, the disclosure of which is also incorporated herein by reference.

TECHNICAL FIELD

The present invention relates to a radiation image detecting system.

BACKGROUND ART

Conventionally, as a medical radiation image obtaining section, a radiation image detecting apparatus, the so-called flat panel detector (FPD), in which solid state image pickup devices are two-dimensionally arranged, has been known. It is known that such a radiation image detecting apparatus is a direct system one, an indirect system one, or the like. The direct system one directly converts radiation energy into electric charges by using a photo conductive material, such as a-Se (amorphous selenium), as a radiation detecting element, and reads out the electric charges as an electric signal pixel by pixel with two-dimensionally arranged signal reading switch elements, such as TFTs (Thin Film Transistors). The indirect system one converts radiation energy into light with a scintillator or the like, converts the light into electric charges with two-dimensionally arranged photoelectric conversion elements, such as photodiodes, and reads out the electric charges as an electric signal with TFTs or the like.

Then, in recent years, a cassette type radiation image detecting apparatus, which incorporates a battery therein and is driven without using any cables so as to be portable, has been developed (see, for example, Patent Documents 1 to 3). When a radiation image detecting apparatus is configured as described above, radiography having a high degree of freedom, including portable radiography at a patient's bedside and the like, becomes possible.

PRIOR ART DOCUMENTS

Patent Documents

Patent Document 1: Japanese Patent Application Laid-Open Publication No. 2001-224579
Patent Document 2: Japanese Patent Application Laid-Open Publication No. Hei 6-342099
Patent Document 3: Japanese Patent No. 3302163

SUMMARY OF THE INVENTION

Problems to Be Solved by the Invention

However, when the radiation image detecting apparatus is driven by an internal battery, it may happen that the battery runs out in process of radiography, transfer processing of image data, or the like. In this case, a disadvantage that the radiography, the transfer processing of image data, or the like must be recommenced is brought about.

Accordingly, it is conceivable that a cable for supplying electric power from the outside to the radiation image detecting apparatus is connected to the radiation image detecting apparatus to perform radiography or the like while charging the battery.

When the battery is charged, it is preferable to complete charging the battery as soon as possible to put the radiation image detecting apparatus in a state in which radiography or the like can be performed without using any cables in order to utilize an advantage of the cassette type radiation image detecting apparatus performing radiography having a high degree of freedom.

However, when it is tried to make a charging current large in order to shorten the charging time, the diameter of the cable for power supply cannot help being thick in order to secure the current-carrying capacity thereof, and a problem of the inconvenience to pull the radiation image detecting apparatus around arises.

Moreover, because the power loss caused by the cable is large and heat generation in a charge controlling circuit and the like becomes large when the charging is performed with a large current, the generated heat influences the characteristics of a sensor panel section of the radiation image detecting apparatus. Furthermore, because the current flowing through the charge controlling circuit becomes large, the noise generated in the charge controlling circuit becomes large in proportion to the current.

Consequently, when it is tried to perform radiography while performing the charging, it is possible that a harmful influence is exerted on an image signal, and a disadvantage such as deterioration of image quality is brought about.

The present invention is made in view of the circumstances described above, and an object of the present invention is to provide a radiation image detecting system charging at high-speed with a large current when only performing the charging, and having a good pulling-around property and causing no deterioration of image quality when performing radiography or the like.

Means for Solving the Problems

In order to settle the aforesaid problems, a radiation image detecting system of the present invention includes:
a cassette type radiation image detecting apparatus capable of being driven by electric power supplied from a built-in battery which supplies the electric power to each of function sections;
a charge controlling circuit to control charging of the battery;
a cradle supplying electric power from an outside to the radiation image detecting apparatus by placing the radiation image detecting apparatus thereon; and
a cable capable of supplying electric power from the outside to the radiation image detecting apparatus by being connected to the radiation image detecting apparatus, wherein
the radiation image detecting apparatus includes a connection section being electrically connected to each of the cradle and the cable to receive the electric power;
the battery is charged by the cradle being connected to the connection section and by the cable being connected to the connection section; and
the charge controlling circuit switches a charging current between a time when the cradle is connected to the connection section and a time when the cable is connected to the connection section.

Effects of the Invention

According to this invention, the current-carrying capacity of the cable can be made to be small by reducing the charging current when the radiation image detecting apparatus is connected to the cable, and consequently the cable can be thinned to improve the pulling-around property of the radiation image detecting apparatus.

Moreover, because the current flowing through the cable and the charge controlling circuit can be made to be small, the power loss for the voltage drop owing to the cable can be reduced, and the heat generation in the charge controlling circuit becomes small and the quantity of noise generated from the charge controlling circuit can be suppressed. Thereby, the deterioration of image quality owing to the heat and the noise can be suppressed.

Furthermore, the radiation image detecting apparatus can be charged with a large current when the radiation image detecting apparatus is connected to the cradle, and has an effect of enabling charging in a short time.

BEST MODE FOR CARRYING OUT THE INVENTION

Figure 1:
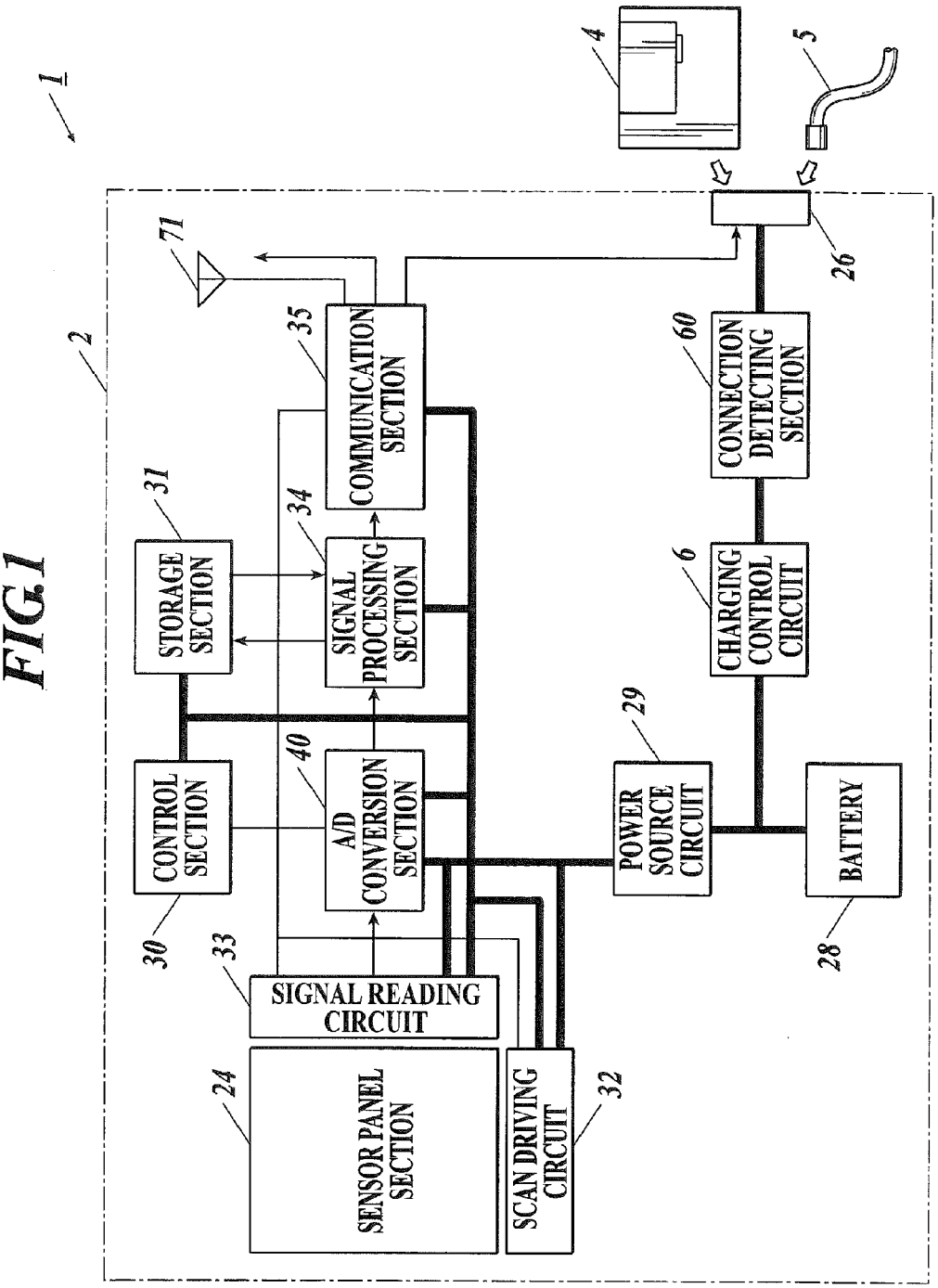
FIG. 1 is a schematic diagram showing the system configuration of a radiation image detecting system according to a first embodiment.

In the following, suitable embodiments of the present invention will be described with reference to the accompanying drawings. Incidentally, the embodiments to which the present invention can be applied are not limited to the embodiments described below.

First Embodiment

A first embodiment of the radiation image detecting system according to the present invention will first be described with reference to FIGS. 1-7. However, the embodiments to which the present invention can be applied are not limited to the ones shown in the drawings.

A radiation image detecting system 1 according to the present embodiment, as shown in FIG. 1, includes a radiation image detecting apparatus 2, a cradle 4 on which the radiation image detecting apparatus 2 is placed, and a cable 5 connected to the radiation image detecting apparatus 2.

Figure 4:
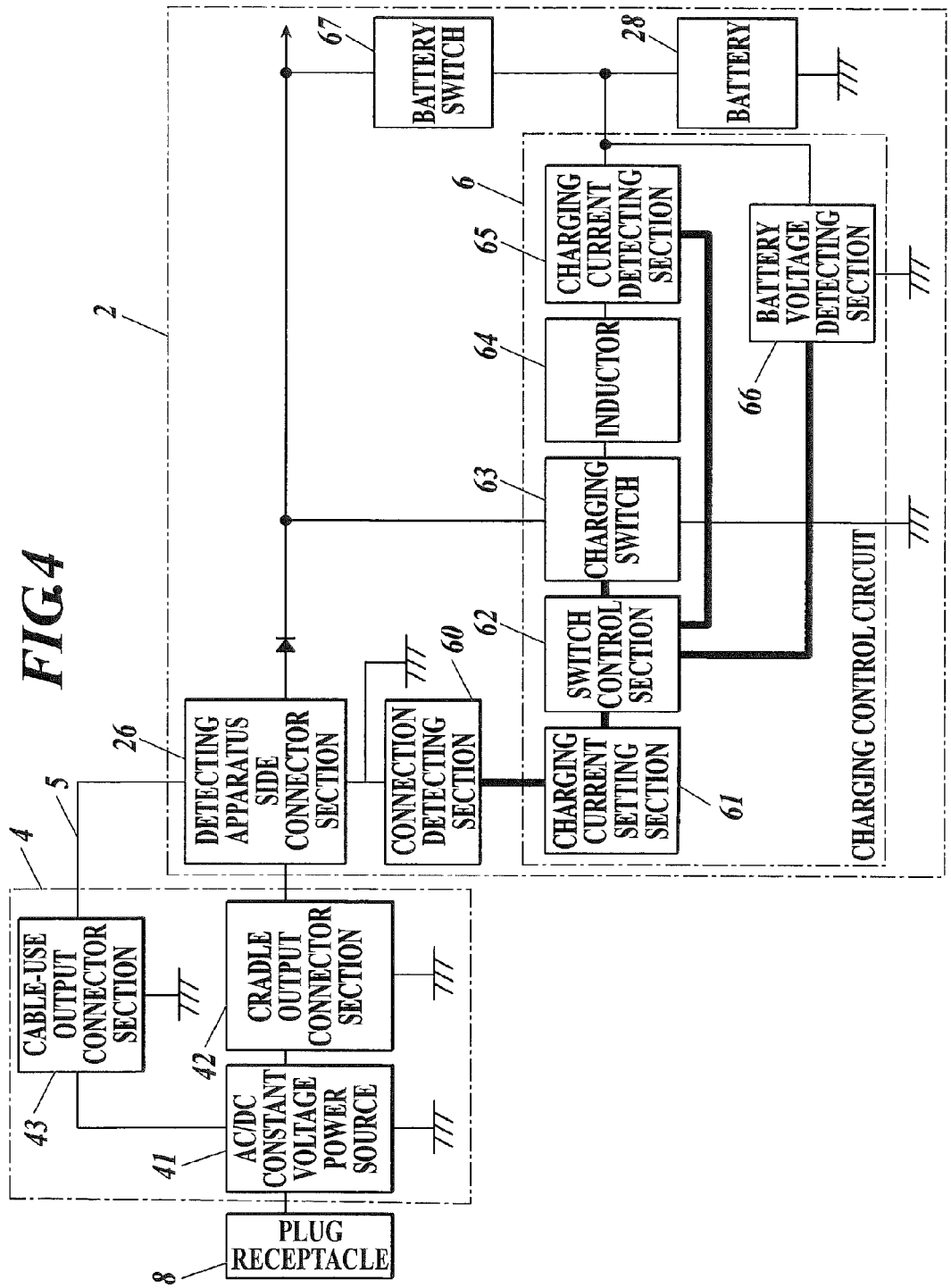
FIG. 4 is a block diagram showing the principal part of the schematic configuration of the charge controlling circuit in FIG. 1.

The cradle 4 supplies electric power to the radiation image detecting apparatus 2 from the outside by placing the radiation image detecting apparatus 2 thereon. As shown in FIG. 4, the cradle 4 includes an AC/DC constant voltage power source 41, to which a plug receptacle 8 to be connected to a not-shown external power source is connected, and output connector sections to output the electric power supplied from the AC/DC constant voltage power source 41 to the outside. The AC/DC constant voltage power source 41 outputs electric power at an always constant voltage independent of the changes of the load thereof, and the output connector sections supply electric power to the radiation image detecting apparatus 2 at this predetermined voltage.

In the present embodiment, the cradle 4 is provided with a cradle output connector section 42 to be connected to a detecting apparatus side connector section 26 when the radiation image detecting apparatus 2 is placed on the cradle 4, and a cable-use output connector section 43, to which the cable 5 to be connected to the detecting apparatus side connector section 26 is connected, as the output connector sections.

When the radiation image detecting apparatus 2 is mounted on the cradle 4, the cradle output connector section 42 is electrically connected to the detecting apparatus side connector section 26 of the radiation image detecting apparatus 2, and electric power is directly supplied from the AC/DC constant voltage power source 41 to the radiation image detecting apparatus 2.

Moreover, when the cable 5 connected to the cable-use output connector section 43 is connected to the detecting apparatus side connector section 26, electric power is supplied from the AC/DC constant voltage power source 41 to the radiation image detecting apparatus 2 through the cable 5.

The cable 5 can supply electric power from the outside to the radiation image detecting apparatus 2 by being connected to the radiation image detecting apparatus 2. In the present embodiment, one end side of the cable 5 is connected to the detecting apparatus side connector section 26 of the radiation image detecting apparatus 2, and the other end side thereof is connected to the cable-use output connector section 43 of the cradle 4. Thereby, electric power is supplied from the AC/DC constant voltage power source 41 to the radiation image detecting apparatus 2.

In the present embodiment, the cable 5 is connected to the external power source through the cradle 4. However, the method of connecting the cable 5 to the external power source is not limited to the aforesaid one. The cable 5 may be directly connected to an AC/DC constant voltage power source existing outside of the cradle 4 to supply electric power from the external power source to the radiation image detecting apparatus 2.

The thickness of the cable 5 is not especially limited. However, in the present embodiment, it is preferable that the diameter of the cable 5 is as thin as possible and the pulling-around thereof is good because it is supposed to perform radiography and the like in the connecting state to the cable 5.

When the diameter of the cable 5 is thin, the current-carrying capacity to be supplied thereto is reduced. However, the power loss for the voltage drop by the cable 5 can be reduced relative to the reduction of the current-carrying capacity. Moreover, the smaller the current-carrying capacity to be supplied is, the smaller the heat generation in a charge controlling circuit 6 described below becomes. Also the deterioration of the image quality owing to the influences by the heat can be suppressed. Moreover, it also becomes possible to suppress the quantity of the noise generated by the charge controlling circuit 6.

The radiation image detecting apparatus 2 in the present embodiment is a portable cassette type FPD, that is to say, a cassette type one of the so-called flat panel detector (hereinafter referred to as "FPD"). The radiation image detecting apparatus 2 is used for radiation image radiography to obtain radiation image data (hereinafter simply referred to as "image data").

Incidentally, although the so-called indirect type radiation image detecting apparatus, which is equipped with a scintillator and the like and obtains an electric signal by converting a radiation into an electromagnetic wave of another wavelength, such as a visible light, will be described as the radiation image detecting apparatus 2 in the following, the present invention can also be applied to the so-called direct type radiation image detecting apparatus to detect a radiation with a radiation detecting device without using the scintillator and the like.

The radiation image detecting apparatus 2 of the present embodiment incorporates a battery 28 therein, as described below. The radiation image detecting apparatus 2 can select one of two driven states between a battery-driven state and an external feeding-driven state. In the battery-driven state, the radiation image detecting apparatus 2 obtains electric power from the battery 28 to drive each of function sections. In the external feeding-driven state, the radiation image detecting apparatus 2 is driven by being supplied with electric power from the outside through the cradle 4 or the cable 5. The radiation image detecting apparatus 2 charges the battery 28 while the driving of each of the function sections in the external feeding-driven state.

Figure 2:
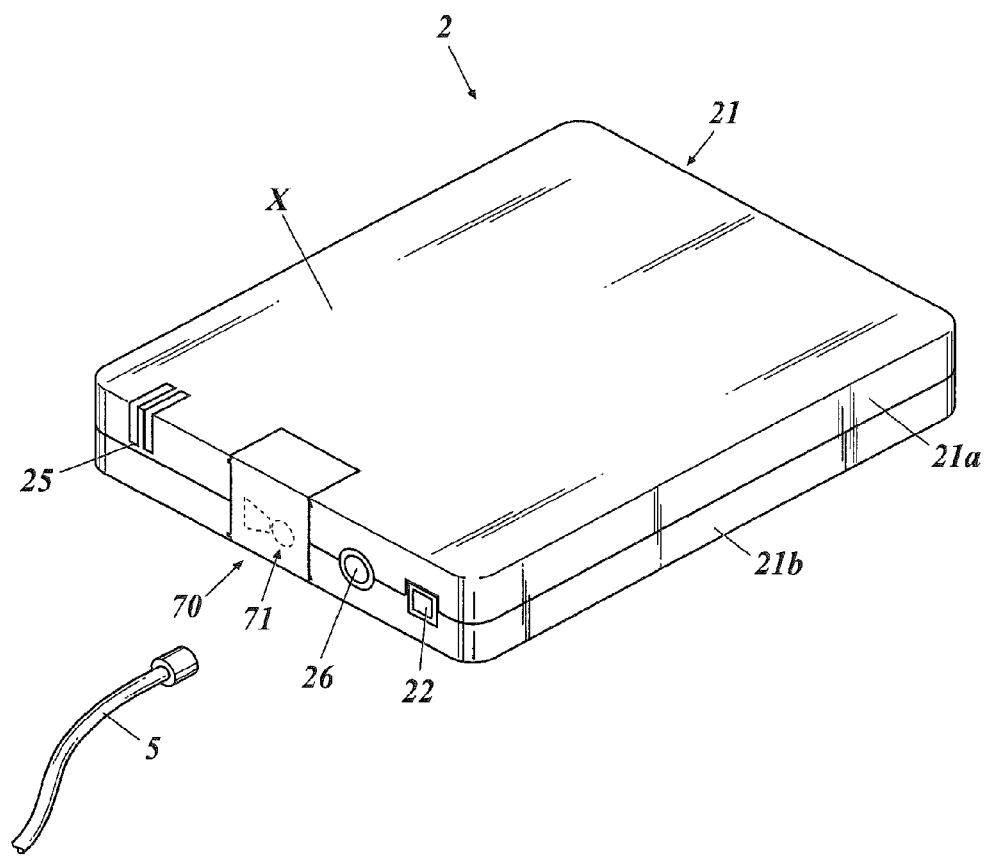
FIG. 2 is a perspective view showing the external appearance of the radiation image detecting apparatus shown in FIG. 1.

FIG. 2 is a perspective view of the radiation image detecting apparatus 2 of the present embodiment.

The radiation image detecting apparatus 2 is equipped with a housing 21 for protecting the inside of the radiation image detecting apparatus 2 as shown in FIG. 2. At least a surface X of the housing 21 on the receiving side of the irradiation of radiation (hereinafter referred to a radiation entering surface X) is made of a material, such as a carbon plate or plastics, which transmits the radiation. Incidentally, although FIG. 2 shows a case where the housing 21 is composed of a front member 21a and a back member 21b, the shape and the configuration of the housing 21 are not especially limited, and it is also possible to form the housing 21 in the cylindrical or so-called monocoque shape.

As shown in FIG. 2, in the present embodiment, an electric power switch 22, an indicator 25, the detecting apparatus side connector section 26, and the like are arranged on a side surface part of the radiation image detecting apparatus 2.

The electric power switch 22 switches the states of being ON/OFF of the power source of the radiation image detecting apparatus 2. An operation of the electric power switch 22 outputs a signal to a control section 30 (see FIG. 1) which will be described below. The signal instructs a start and a stop of power supply to each of the function sections of the radiation image detecting apparatus 2 by the battery 28 (see FIG. 1) which will be described below. When the radiation image detecting apparatus 2 is not used for radiography, the electric power consumption of the battery 28 can be suppressed by setting the power source OFF (that is, stopping the power supply by the battery 28 to each of the function sections).

The indicator 25 is made of, for example, an LED or the like, and displays the residual quantity of the charge of the battery 28, various operation situations, and the like.

Moreover, the radiation image detecting apparatus 2 is provided with the battery 28 to supply electric power to each of the function sections of the radiation image detecting apparatus 2.

The battery 28 is a chargeable one, and, for example, a rechargeable secondary battery, such as a nickel cadmium rechargeable battery, a nickel hydrogen battery, a lithium ion battery, a small-sized sealed lead-acid battery, and a lead acid battery; an electric storage element, such as an electric double layer capacitor and a lithium ion capacitor (LIC); and the like can be applied as the battery 28.

Among them, the lithium ion capacitor is especially excellent in electric storage efficiency, and can be charged with a large current (for example, 5-10 amperes) at a high speed to enable a charging time to be greatly shortened. Consequently, the lithium ion capacitor is preferable.

Moreover, a cover member 70 that is opened and closed for exchanging the battery 28 incorporated in the housing 21 is provided on the side surface part of the radiation image detecting apparatus 2. An antenna device 71 for the radiation image detecting apparatus 2 to perform transmission and reception of information with the outside by a wireless system through a wireless access point 113 (see FIG. 5) which will be described below is embedded in a side surface part of the cover member 70.

The detecting apparatus side connector section 26 is, as shown in FIG. 4, a connection section which is electrically connected to each of the cradle 4 and the cable 5 to perform power reception of electric power supplied from the outside to the radiation image detecting apparatus 2.

As described below, when the cradle output connector section 42 of the cradle 4 is connected to the detecting apparatus side connector section 26, it becomes possible to supply a large current to the battery 28 to rapidly charge the battery 28. Moreover, when the cable 5 is connected to the detecting apparatus side connector section 26, it becomes possible to charge the battery 28 while driving each of the function sections by the electric power supplied from the outside.

A connection detecting section 60 is provided between the battery 28 and the detecting apparatus side connector section 26. The connection detecting section 60 is detection section for detecting which of the cradle 4 and the cable 5 is connected to the detecting apparatus side connector section 26. A detection result of the connection detecting section 60 is output to a charging current setting section 61 of the charge controlling circuit 6.

Incidentally, in the present embodiment, the technique by which the connection detecting section 60 detects which of the cradle 4 and the cable 5 is connected to the detecting apparatus side connector section 26 is not especially limited. A mechanical switch (not shown) to the detecting apparatus side connector section 26 may switch the ON/OFF state in accordance with the connection of the cradle 4 or the connection of the cable 5. Also a detecting contact point may switch the contacting/non-contacting state in accordance with the connection of the cradle 4 or the connection of the cable 5.

Moreover, a power source circuit 29 (see FIG. 1) is provided between the battery 28 and the function sections. The power source circuit 29 is a function section to suitably convert and adjust the current value and the like of the electric power supplied from the battery 28 in order to be fitted to each of the function sections of battery supply destinations.

A not-shown scintillator layer formed inside the radiation entering surface X of the housing 21 (see FIG. 2). The scintillator layer absorbs the radiation entering the scintillator layer from the radiation entering surface X to convert the radiation into light of which the wavelengths includes those of visible light. As the scintillator layer, for example, one formed by using a phosphor such as CsI:Tl, $Gd_2O_2S$:Tb, and ZnS:Ag, in which a light emission center material is attached to and activated in a parent body, can be used.

A sensor panel section 24 as the detection section is provided on the surface side of the scintillator layer, the surface side being opposite to the surface which the radiation enters. A plurality of photoelectric conversion elements 23 (see FIG. 3) is two-dimensionally arranged in the sensor panel section 24. Each photoelectric conversion elements 23 converts the light output from the scintillator layer into an electric signal. Each of the photoelectric conversion elements 23 is, for example, a photodiode or the like, and constitutes the radiation detecting device, converting the radiation that has passed through a subject into an electric signal, together with the scintillator layer and the like.

In the present embodiment, a reading section 45 (see FIG. 3), which is reading section for reading an output value of each of the photoelectric conversion elements 23 in the sensor panel section 24, is composed of the control section 30, a scan driving circuit 32, a signal reading circuit 33, and the like.

The configurations of the sensor panel section 24 and the reading section 45 will further be described with reference to the equivalent circuit diagram of FIG. 3.

Figure 3:
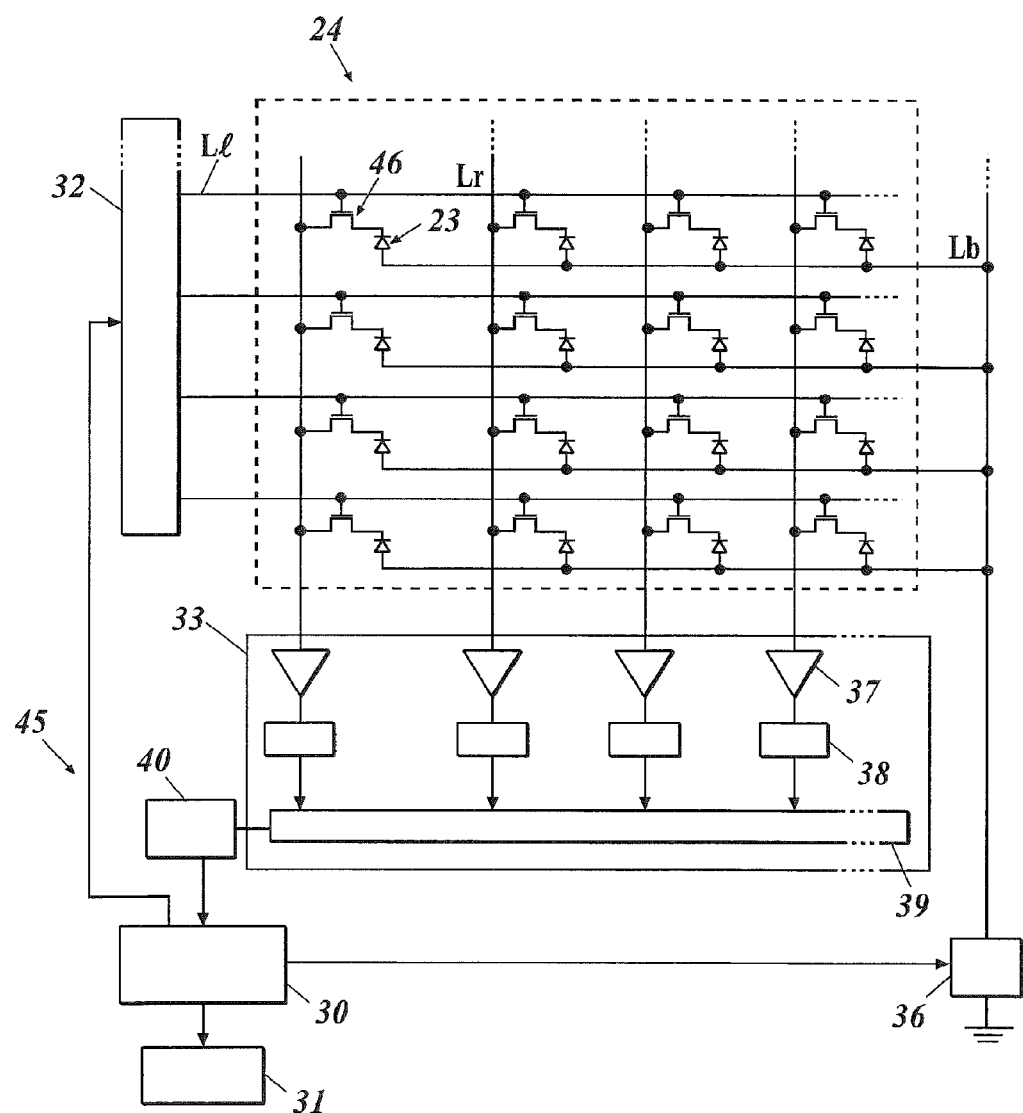
FIG. 3 is an equivalent circuit diagram showing the configuration of the sensor panel section, the reading section, and the like of the radiation image detecting apparatus shown in FIG. 1.

As shown in FIG. 3, the source electrode of each of TFTs 46, which are signal reading switch elements, is connected to one electrode of each of the photoelectric conversion elements 23 in the sensor panel section 24. Moreover, a bias line Lb is connected to the other electrode of each of the photoelectric conversion elements 23, and the bias line Lb is connected to a bias power source 36. Thereby, a reverse bias voltage is applied from the bias power source 36 to each of the photoelectric conversion elements 23.

The gate electrode of each of the TFTs 46 is connected to each of scanning lines L1 extending from the scan driving circuit 32. A read voltage (ON voltage) or an OFF voltage is applied from a not-shown TFT power source to the gate electrode of each of the TFTs 46 through each of the scanning lines L1. Moreover, the drain electrode of each of the TFTs 46 is connected to each of signal lines Lr. Each of the signal lines Lr is connected to each of amplifier circuits 37 in the signal reading circuit 33. The output line of each of the amplifier circuits 37 is connected to an analog multiplexer 39 through each of sample hold circuits 38. Moreover, an A/D conversion section 40 as processing section for performing converting a signal into a digital signal is connected to the signal reading circuit 33. An analog image signal transmitted from the analog multiplexer 39 is converted into a digital image signal by the A/D conversion section 40. The signal reading circuit 33 is connected to the control section 30 through the A/D conversion section 40. The digital image signal is output to the control section 30. A storage section 31 is connected to the control section 30. The control section 30 makes the storage section 31 store the digital image signal transmitted from the A/D conversion section 40 as image data.

The control section 30 is a computer including a CPU (Central Processing Unit), a ROM (Read Only Memory), and a RAM (Random Access Memory), which are not shown. The control section 30 collectively controls the whole of the radiation image detecting apparatus 2.

A signal processing section 34 is a function section to make the image data be data of the format fitted to be output to the outside by predetermined signal processing to the image data.

The ROM stores programs for performing various processing at the radiation image detecting apparatus 2, the processing such as radiographed image data generation processing, offset correction value generation processing and power supply control processing; various control programs; parameters; and the like.

The control section 30 reads a prescribed program from the ROM, the program which is stored therein, expands the program in a work area of the RAM, and performs processing according to the program.

The storage section 31 is composed of a HDD (Hard Disk Drive), a flash memory, or the like, and stores radiographed image data (image data based on a radiation passing through a subject) generated by the reading section (shown in FIG. 3), dark reading values (image data obtained without irradiation), offset correction values, and the like.

The storage section 31 may be a built-in memory or a removable memory such as a memory card. The capacity of the storage section 31 is not limited. However, it is preferable that the storage section 31 have the capacity which can store image data of a plurality of images. Having such a storage section makes it possible to successively irradiate a subject, and record and accumulate image data each time the subject is irradiated. As a result, seriography and video shooting become available.

The communication section 35 is connected to the antenna device 46, and transmits and receives various signals to/from an external device such as the console 101 according to control of the control section 30. The communication section 35 communicates with an external device such as the console 101 via the wireless access point 113 by a wireless method.

In the embodiment of the present invention, the communication section 35 transmits image data (radiographed image data or data obtained by the dark reading) to the console 101, which is an external device, based on an image signal read by the reading section 45, and also receives radiography order information from the console 101 or the like.

The charge controlling circuit 6 is a function section to control a charging current supplied to the battery 28 when the battery 28 is charged. FIG. 4 is a block diagram of the charge controlling circuit 6 in the present embodiment.

As shown in FIG. 4, the charge controlling circuit 6 in the present embodiment includes the charging current setting section 61, a switch control section 62, a charging switch 63, an inductor 64, a charging current detecting section 65, and a battery voltage detecting section 66.

The charging current setting section 61 is a function section to switch the charging current supplied to the battery 28 in accordance with a detection result by the connection detecting section 60.

In the present embodiment, the value of the charging current supplied to the battery 28 is set high to charge the battery 28 at high-speed by a large current when it is detected that the cradle output connector section 42 is connected to the detecting apparatus side connector section 26.

Moreover, the current value of the current supplied to the battery 28 is set low to charge the battery 28 with a small current when it is detected that the cable 5 is connected to the detecting apparatus side connector section 26. Radiography and the like are performed while charging the battery 28 in this case, and the electric power is supplied from the external power source through the cable 5 to each of the function sections besides the battery 28 through the power source circuit 29.

The battery voltage detecting section 66 is a function section to detect the voltage of the battery 28. The battery voltage detecting section 66 outputs a detection result detected thereby to the switch control section 62.

The charging current detecting section 65 is a function section to detect the current value of a charging current to be supplied to the battery 28 for charging the battery 28 when the battery 28 is charged. The charging current detecting section 65 detects a change of the current value of the current to be supplied to the battery 28 to output the detected result to the switch control section 62.

As described below, in the present embodiment, the charging system is switched to constant voltage charging after constant current charging to a certain degree when charging the battery 28. When the charging system is switched from the constant current charging to the constant voltage charging, the current flowing to the battery 28 gradually decreases as the time elapses. The charging current detecting section 65 detects the change of the current value and outputs the detected result to the switch control section 62.

The charging switch 63 is a switch for controlling a charging current or a charging voltage to the battery 28.

In the present embodiment, performs the constant current charging is performed at first to supply a current at a predetermined current value to the battery 28 when charging the battery 28. When the constant current charging is started, the voltage of the battery 28 gradually increases as the time elapses. That is, charging is performed while the voltage is gradually increased in order to keep a constant current value. However, if the constant current charging is continued as it is after the voltage of the battery 28 has exceeded a predetermined voltage, the current flows much and hence exceeds the capacity. Therefore, in the present embodiment, the constant current charging is performed until the voltage of the battery 28 reaches a predetermined threshold value, and the charging system is switched to the constant voltage charging after the voltage of the battery 28 has reached the predetermined threshold value. Then, the constant voltage charging charges the battery 28 to the very limit of the capacity thereof, and stops the charging when the battery 28 is fully charged.

The charging switch 63 is a function section to perform such switching in conformity with the control of the switch control section 62.

Incidentally, as the charging switch 63, an FET is generally used, but the charging switch 63 may be composed of any of an electromagnetic switch (electromagnetic relay), a semi-conductor switch (solid-state relay; SSR), a photoelectric switch (photo-relay), and the like.

The switch control section 62 is a function section to control the charging switch 63. The switch control section 62 is connected to the battery voltage detecting section 66. The switch control section 62 controls the charging switch 63 to perform the constant current charging until the voltage of the battery 28 reaches the predetermined value (threshold value). The switch control section 62 controls the charging switch 63 to switch from the constant current charging to the constant voltage charging after the voltage of the battery 28 reaches the predetermined value or more.

Moreover, the switch control section 62 controls the charging switch 63 to be turned off to stop the charging of the battery 28 when the battery 28 becomes a fully charged state by the constant voltage charging. To put it concretely, the switch control section 62 receives the output of a detection result from the charging current detecting section 65, as described above. The switch control section 62 judges that the charging has ended when almost no current has flown (at the time point when the current value has become the predetermined threshold value or less) on the basis of the detection result from the charging current detecting section 65, and to turn off the charging switch 63.

Moreover, the inductor 64 is provided in the charge controlling circuit 6. The current transmitted from the AC/DC constant voltage power source 41 is supplied to the battery 28 through the inductor 64. The inductor 64 smoothes the voltage and the current when the charging switch 63 is turned on or off.

Moreover, a battery switch 67 to switch the ON/OFF of the charging of the battery 28 is provided between the charge controlling circuit 6 and the battery 28. The battery switch 67 has the function of preventing the inflow of a current from a part other than the charge controlling circuit 6 into the battery 28 and of breaking the connection of the battery 28 and a load at the time of charging and at the time of overdischarging.

Figure 5:
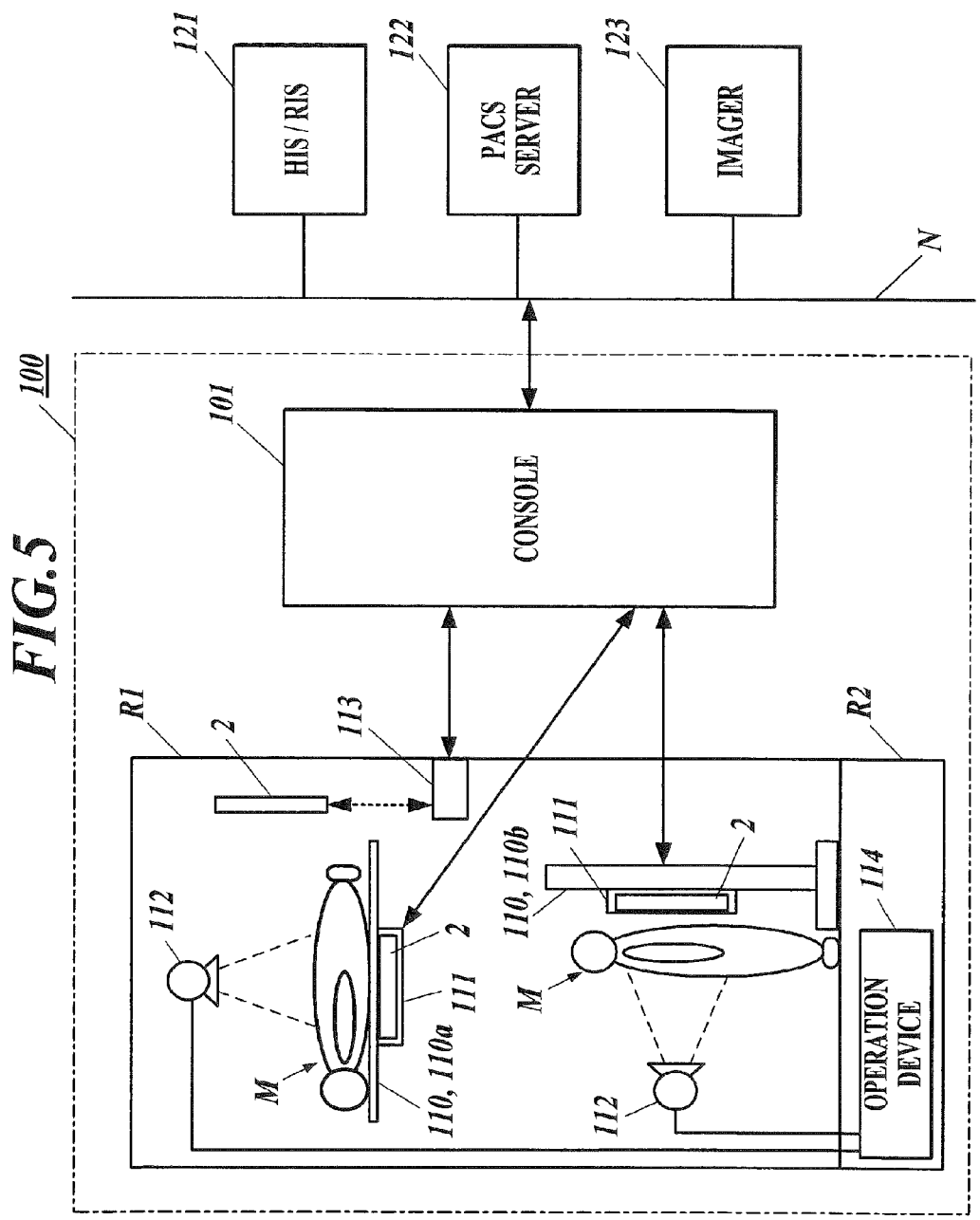
FIG. 5 is a schematic diagram showing an example of the system configuration of a radiation image radiographing system to which the radiation image detecting system is applied.

Incidentally, the radiation image detecting system 1 is used, for example, by being arranged in a radiation image radiographing system 100 as shown in FIG. 5.

The radiation image radiographing system 100 is equipped with, for example, the radiation image detecting system 1 and the console 101 capable of communicating with the radiation image detecting apparatus 2 constituting the radiation image detecting system 1.

As shown in FIG. 5, the radiation image detecting apparatus 2 is provided, for example, in a radiography room R1 where a subject (a region to be radiographed of a patient) which is a region of a patient is radiographed by irradiation, and the console 101 is provided for the radiography room R1.

In the embodiment of the present invention, there is one radiography room R1 in the radiography system, and three radiation image detecting apparatus 2 are disposed in the radiography room R1, which is a case to be described as an example. However, the number of radiography rooms and the number of radiation image detecting apparatus 2 in the respective radiography rooms are not limited to the drawings.

Furthermore, when there is a plurality of radiography rooms R1, the console 101 is not necessarily provided for each of the radiography rooms R1. One console 101 may be provided for the plurality of radiography rooms R1.

Bucky devices 110 and radiation generators 112 are provided in the radiography room R1. Each of the Bucky devices 110 includes a cassette holding section 111 into which the radiation image detecting apparatus 2 can be loaded or which can hold the radiation image detecting apparatus 2. Each of the radiation generators 112 includes a radiation source (not shown) such as an X-ray tube which irradiates a subject (a region to be radiographed of a patient M). The cassette holding section 111 is a section into which the Radiation image detecting apparatus 2 is loaded at the time of radiography.

FIG. 5 shows a case where one Bucky device 110a for radiography in the decubitus position and one Bucky device 110b for radiography in the standing position are provided in the radiography room R1. However, the number of Bucky devices 110 in the radiography room R1 is not limited thereto. Furthermore, in the embodiment of the present invention, the radiation generators 112 are provided with the Bucky devices 110, respectively. However, for example, one radiation generator 112 may be provided for a plurality of Bucky devices 110 in the radiography room R1, and be used by appropriately changing the position of the radiation generator 112, by changing the direction of irradiation thereof, and the like.

The radiography room R1 is a room which blocks radiations, and radio waves for wireless communications are blocked, accordingly. Therefore, a wireless access point (base station) 113 or the like is provided in the radiography room R1, the wireless access point 113 through which communications between the Radiation image detecting apparatus 2 and an external device such as the console 101 are performed when the Radiation image detecting apparatus and the external device such as the console 101 communicate with each other.

In addition, a preparation room R2 is provided next to the radiography room R1 in the embodiment of the present invention. In the preparation room R2, an operation device 114 is placed, the operation device 114 by which a radiologist, a doctor, or the like (hereinafter referred to as "operator") controls a tube voltage, a tube current, an irradiation-field diaphragm, and the like of the radiation generator 112 which irradiates a subject, and operates the Bucky device 110, and the like.

A control signal for controlling an irradiation condition of the radiation generator 112 is transmitted from the console 101 to the operation device 114. The irradiation condition for the radiation generator 112 is set according to the control signal transmitted from the console 101 to the operation device 114. The irradiation condition includes a start/end timing of irradiation, a value of the radiation tube current, a value of the radiation tube voltage, and a filter type.

An irradiation instruction signal which instructs irradiation is transmitted from the operation device 114 to the radiation generator 112. The radiation generator 112 irradiates a prescribed radiation at a prescribed timing for a prescribed duration in accordance with the irradiation instruction signal.

The console 101 is a computer equipped with a control section composed of a CPU (Central Processing Unit) or the like, a storage section, an input section, a display section, a communication section (all being not shown), and the like.

The console 101 makes the display section display the image based on image data transmitted from the radiation image detecting apparatus 2, and performs various kinds of image processing to this image data.

In the present embodiment, the console 101 is connected to external devices, such as an HIS/RIS 121, a PACS server 122, and an imager 123, through a network N.

Next, the operation of the radiation image detecting system 1 in the present embodiment will be described with reference to FIGS. 6 and 7.

Figure 6:
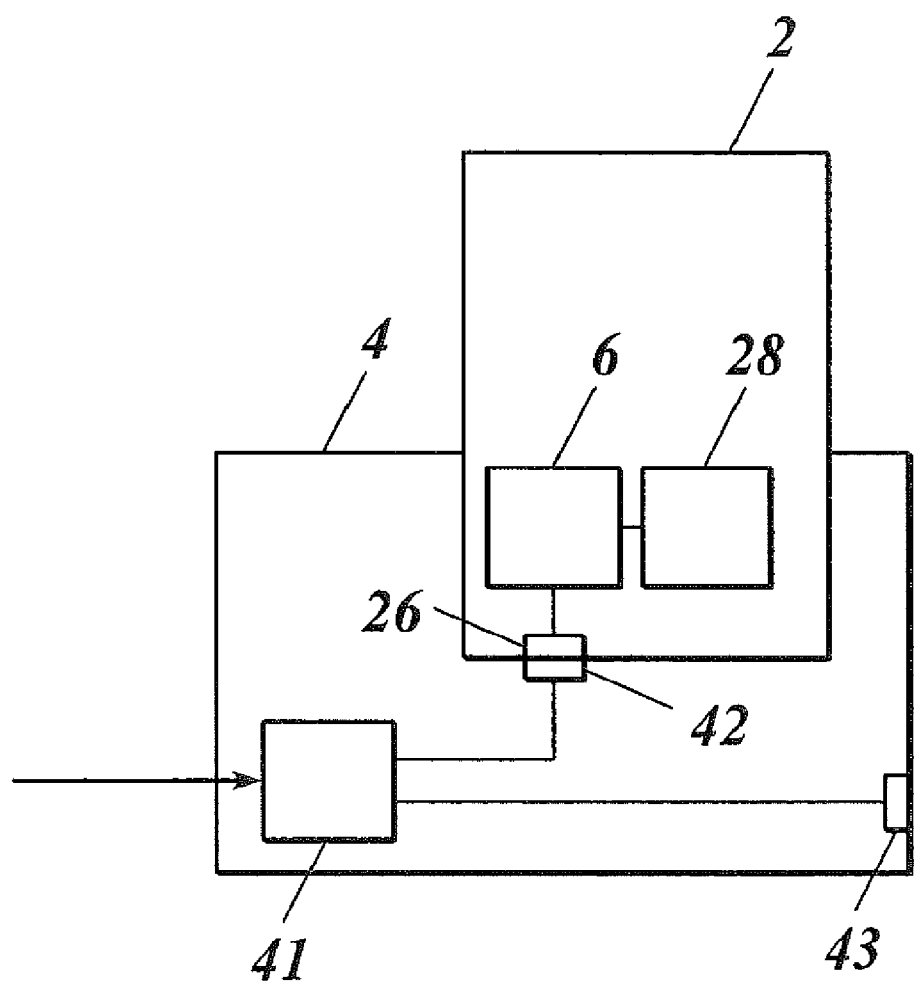
FIG. 6 is an explanatory diagram showing the connection state of the radiation image detecting apparatus shown in FIG. 1 with the cradle.

FIG. 6 is a view schematically showing the state in which the radiation image detecting apparatus 2 is mounted on the cradle 4.

When the radiation image detecting apparatus 2 is mounted on the cradle 4, the connection of the cradle output connector section 42 to the detecting apparatus side connector section 26 is detected by the connection detecting section 60. The detection result by the connection detecting section 60 is output to the charging current setting section 61 of the charge controlling circuit 6 provided in the radiation image detecting apparatus 2.

When the detection result is transmitted from the connection detecting section 60 to the charging current setting section 61, the charging current setting section 61 sets the value of the charging current to be supplied to the battery 28 to large, for example, 2 amperes, in order to charge the battery 28 with the large current according to the detection result. The set result by the charging current setting section 61 is output to the switch control section 62. The detection result of the voltage of the battery 28 is output from the battery voltage detecting section 66 to the switch control section 62. The value of the charging current flowing into the battery 28 is output from the charging current detecting section 65 to the switch control section 62. The switch control section 62 judges whether it is needed or not to charge the battery 28 on the basis of the results output from these battery voltage detecting section 66 and charging current detecting section 65. When the switch control section 62 judges that the charging is needed, the switch control section 62 turns on the charging switch 63 and controls the charging switch 63 in order to perform the charging with the current value (for example 2 amperes) set by the charging current setting section 61. Thereby, a constant current charging of the constant current value (for example, set current value of 2 amperes) is started.

During the charging, detection results are output from the battery voltage detecting section 66 and the charging current detecting section 65 to the switch control section 62 as needed, and the switch control section 62 always judges which of the constant current charging and the constant voltage charging should be performed and whether the charging should be continued or ended on the basis of the detection results. Then, when the voltage of the battery 28 output from the battery voltage detecting section 66 reaches a predetermined value or more, the switch control section 62 controls the charging switch 63 in order to switch the constant current charging to the constant voltage charging.

Moreover, when the current value output from the charging current detecting section 65 reaches a predetermined value or less, the switch control section 62 judges that the charging should be ended, and controls the charging switch 63 to be switched off. Thereby, the charging of the battery 28 ends.

Figure 7:
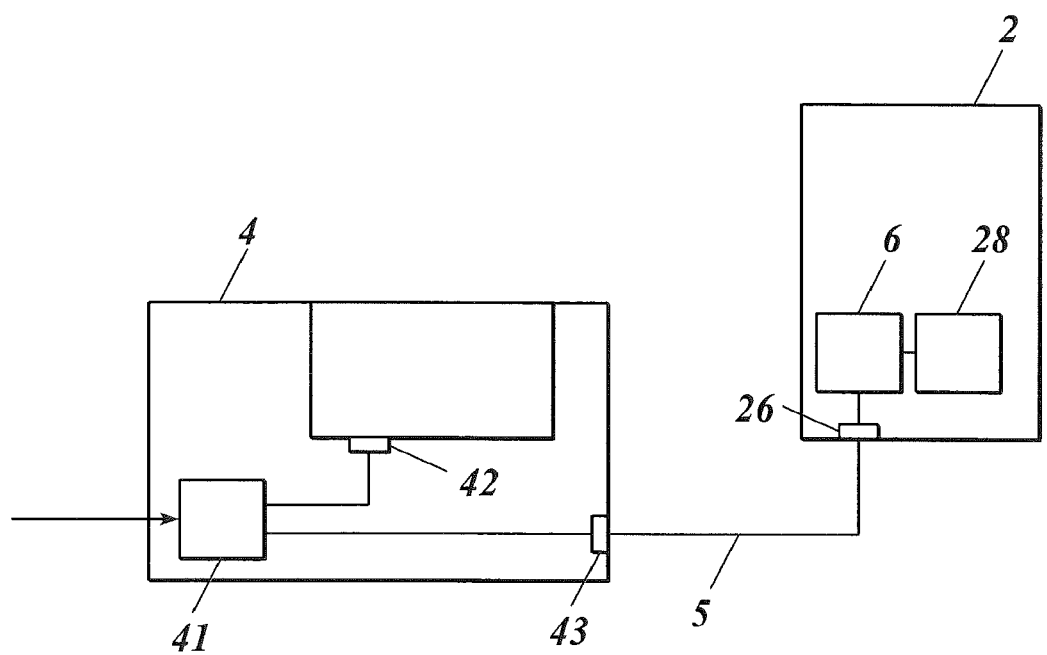
FIG. 7 is an explanatory diagram showing the connection state to the radiation image detecting apparatus shown in FIG. 1 with the cable.

Next, FIG. 7 is a view schematically showing the state in which the cable 5 is connected to the radiation image detecting apparatus 2.

When the cable 5 connected to the cable-use output connector section 43 of the cradle 4 is connected to the detecting apparatus side connector section 26 of the radiation image detecting apparatus 2, the connection is detected by the connection detecting section 60. The detection result by the connection detecting section 60 is output to the charging current setting section 61 of the charge controlling circuit 6.

When the detection result is transmitted from the connection detecting section 60 to the charging current setting section 61, the charging current setting section 61 sets the value of the charging current to small, such as 0.1 amperes, in order to charge the battery 28 with the small current according to the detection result. The set result by the charging current setting section 61 is output to the switch control section 62. The detection result of the voltage of the battery 28 is output from the battery voltage detection section 66 to the switch control section 62, and the value of the charging current flowing into the battery 28 is output from the charging current detecting section 65 to the switch control section 62. The switch control section 62 judges whether the charging of the battery 28 is needed or not on the basis of the results output from these battery voltage detecting section 66 and charging current detecting section 65. When the switch control section 62 judges that the charging is needed, the switch control section 62 controls the charging switch 63 in order to perform the charging with the current value (for example, 0.1 amperes) set by the charging current setting section 61. Thereby, the constant current charging with the current value of 0.1 amperes is started.

Moreover, in this case, radiography, data processing, and the like can be performed while the charging of the battery 28 is performed, and electric power is supplied from the battery 28 or an external power source through the detecting apparatus side connector section 26 to each of the function sections of the radiation image detecting apparatus 2. When radiography and the like are performed while charging is performed, the whole current value to be supplied becomes larger since the power is supplied to each of the function sections at the same time.

During charging, the detection results are output from the battery voltage detecting section 66 and the charging current detecting section 65 to the switch control section 62 as needed, and the switch control section 62 always judges which of the constant current charging and the constant voltage charging should be performed and whether the charging should be continued or ended on the basis of the detection results. Then, when the voltage of the battery 28 output from the battery voltage detecting section 66 becomes the predetermined value or more, the switch control section 62 controls the charging switch 63 in order to switch the constant current charging to the constant voltage charging.

Moreover, when the current value output from the charging current detecting section 65 reaches the predetermined value or less, the switch control section 62 judges that the charging should be ended, and controls the charging switch 63 to be switched off. Thereby, the charging of the battery 28 ends.

As described above, according to the present embodiment, when the cradle output connector section 42 is connected to the detecting apparatus side connector section 26, high-speed charging can be performed with a large current. When the cable 5 is connected to the detecting apparatus side connector section 26, the processing of radiography and the like can be performed while charging is performed with a small current.

When the cable 5 is connected to the detecting apparatus side connector section 26, the charging current is made to be small. Consequently, the current-carrying capacity of the cable 5 can be made to be small, and the cable 5 can be thinner. Thereby, the property to pull the radiation image detecting apparatus 2 around is improved, and radiography and the like can easily be performed without being anxious about the residual quantity of the battery 28 while the charging of the battery 28 is being performed.

Moreover, because the current flowing through the cable 5 is made to be small, the power loss for the voltage drop owing to the cable 5 can be reduced.

Moreover, when the cable 5 is connected to the detecting apparatus side connector section 26, charging is performed with a small current, and consequently heat generation of the charge controlling circuit 6 becomes small, thereby the deterioration of the image quality owing to the influences of heat is suppressed. Moreover, because it is possible to suppress the quantity of noise generated from the charge controlling circuit 6, the influences of the image quality owing to charging can be suppressed.

Moreover, when the cradle output connector section 42 is connected to the detecting apparatus side connector section 26, radiography performed in the connecting state is not possible. Consequently it is unnecessary to be anxious about the influences owing to the heat generation and the generation of noise by charging. Accordingly, in such a state, short time charging can be performed with a large current.

Incidentally, although the present embodiment provides the cradle output connector section 42 and the cable-use output connector section 43 separately from each other in the cradle 4, the output connector sections of the cradle 4 are not limited to such a configuration.

Figure 8:
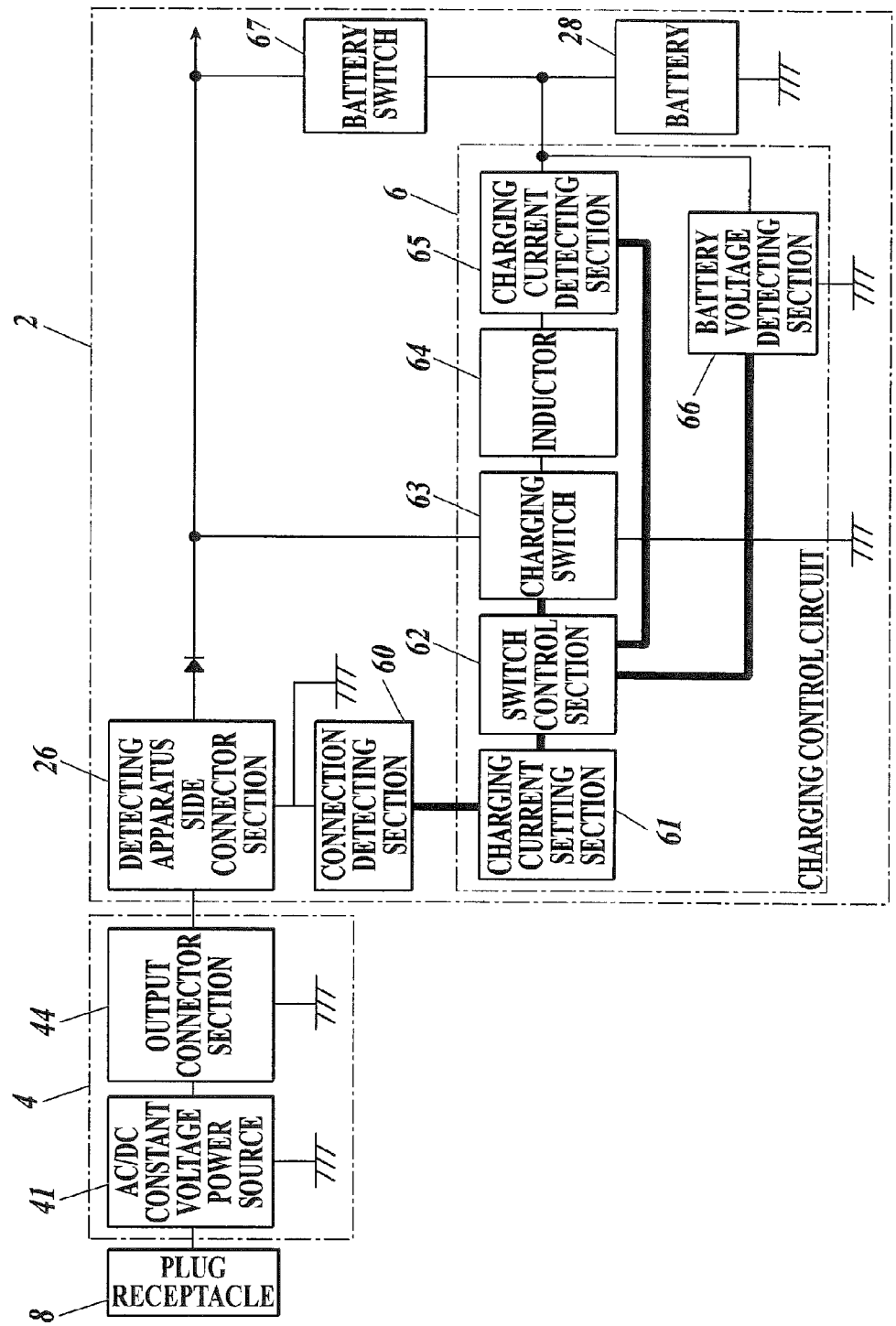
FIG. 8 is a block diagram showing the principal part of a modification of the connector section of the cradle as shown in FIG. 4.

For example, as shown in FIG. 8, the configuration in which one output connector section 44 may be provided in the cradle 4 for the connection by the mounting of the cradle 4 and the connection by the cable 5.

In the present embodiment, an example that processing of radiography and the like are performed while charging of the battery 28 is performed has been described. However, the processing when the cable 5 is connected to the detection apparatus side connector section 26 is not limited to this mode.

For example, the supply of the electric power received from an external power source to the battery 28 may be controlled according to the working state of each of the function sections of the radiation image detecting apparatus 2; for example, when the processing of radiography, the transmission of image data, or the like is being performed and the cable 5 is connected to the detecting apparatus side connector section 26, the charging of the battery 28 may not be performed.

Moreover, in the present embodiment, the radiation image detecting apparatus 2 communicates with an external device, such as the console 101, through the antenna device 71 by a wireless system. However, for example, a connector section for communication may be provided to communicate with the external device by a wired system when a cable for communication is connected to the connector section.

In this case, the connector section (the detecting apparatus side connector section 26, the cradle output connector section 42, and the cable-use output connector section 43) for power supply may furthermore be used as the connector section for communication.

In the present embodiment, the operation device 114 is provided in the preparation room R2, and the console 101 to control the radiography system 100 as a whole is provided separately therefrom. However, the console 101 may be provided for each preparation room R2 instead of the operation device 114. In this case, in addition to controlling the radiography system 100 as a whole, the console 101 controls the radiation generator 112, operates the Bucky device 110, and the like, as needed.

In addition, it is needless to say that the present invention is not limited to the present embodiment, and can suitably be changed.

Second Embodiment

Next, a second embodiment of the present invention will be described with reference to FIGS. 9-11. Incidentally, the second embodiment is different from the first embodiment in the configuration of a charge controlling circuit to control the charging of a battery, and the point different from that of the first embodiment will especially be described in the following.

Figure 9:
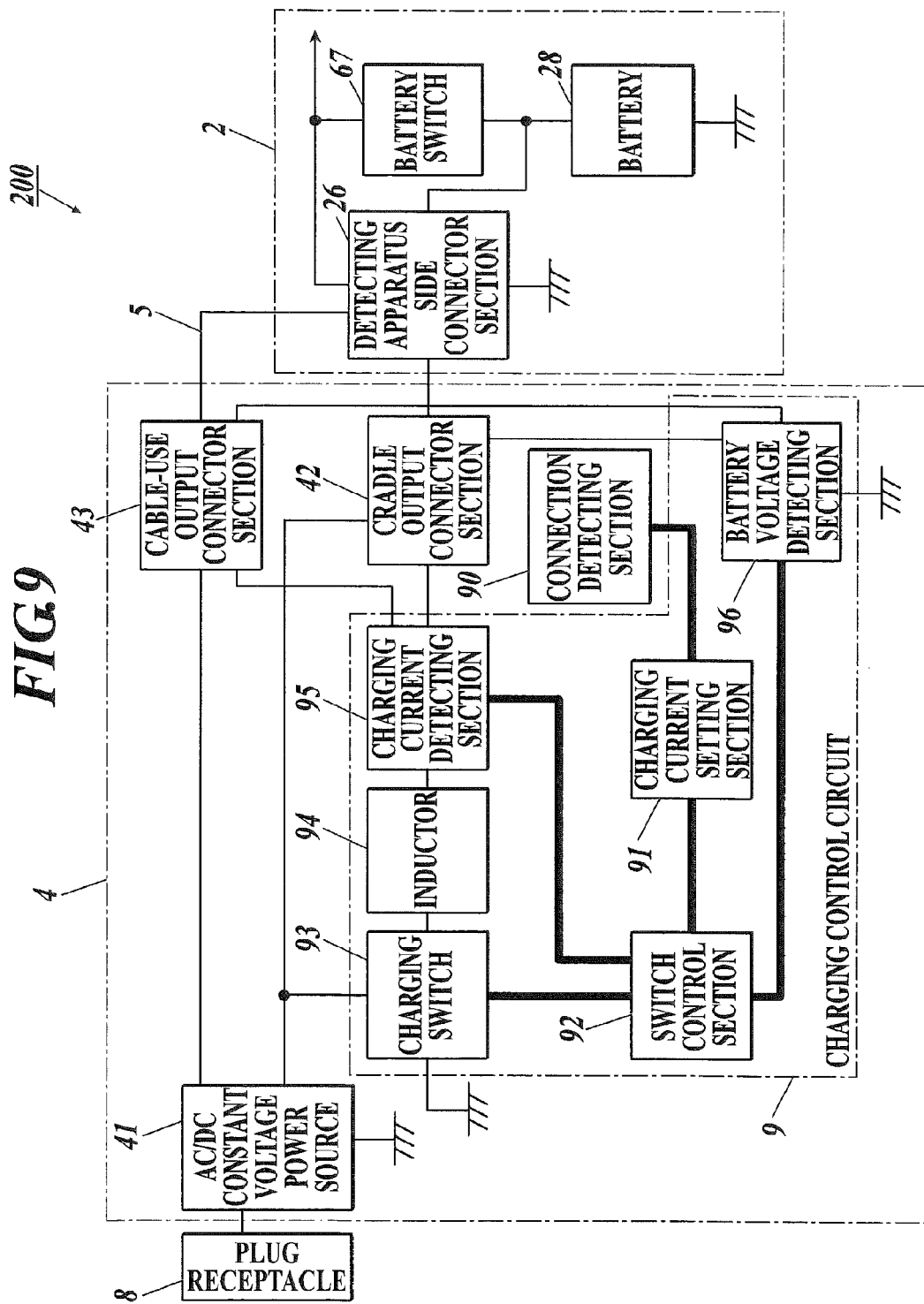
FIG. 9 is a block diagram showing the principal part of the schematic configuration of a charge controlling circuit in the radiation image detecting system according to a second embodiment.

As shown in FIG. 9, a radiation image detecting system 200 is equipped with the radiation image detecting apparatus 2, the cradle 4, and the cable 5 in the present embodiment similarly to the first embodiment.

The cradle 4 is provided with a charge controlling circuit 9 equipped with a charging current setting section 91, a switch control section 92, a charging switch 93, an inductor 94, a charging current detecting section 95, and a battery voltage detecting section 96. The charge controlling circuit 9 performs the setting of the current value of a charging current to be supplied to the battery 28 and the like when the battery 28 of the radiation image detecting apparatus 2 is being charged. Incidentally, the configuration of each of the function sections constituting the charge controlling circuit 9 is similar to that thereof in the first embodiment, and the description thereof is accordingly omitted.

A connection detecting section 90 as detection section is connected to the charge controlling circuit 9. The connection detecting section 90 detects which of the cradle output connector section 42 and the cable 5 connected to the cable-use output connector section 43 is connected to the detecting apparatus side connector section 26 of the radiation image detecting apparatus 2, and outputs the detection result to the charging current setting section 91 of the charge controlling circuit 9.

The charging current setting section 91 sets the current value of a current to be supplied to the battery 28 when charging the battery 28 on the basis of the detection result of the connection detecting section 90.

Moreover, the voltage of the battery 28 detected by the battery voltage detecting section 96 and the value of the charging current detected by the charging current detecting section 95 are output to the switch control section 92, and the switch control section 92 controls the charging switch 93 on the basis of these detection results. The switch control section 92 controls the charging switch 93 to supply the current having a current value to the battery 28 through the detecting apparatus side connector section 26. The current value corresponds to the distinction between the charging by a cradle connection and the charging by a cable connection, the specification or a charged state of the battery 28, and the like.

The configuration of the other parts of the radiation image detecting system 200 is similar to those shown in the first embodiment. Accordingly, the same parts are denoted by the same marks, and their descriptions are omitted.

Next, the operation of the radiation image detecting system 200 in the present embodiment will be described with reference to FIGS. 10 and 11.

Figure 10:
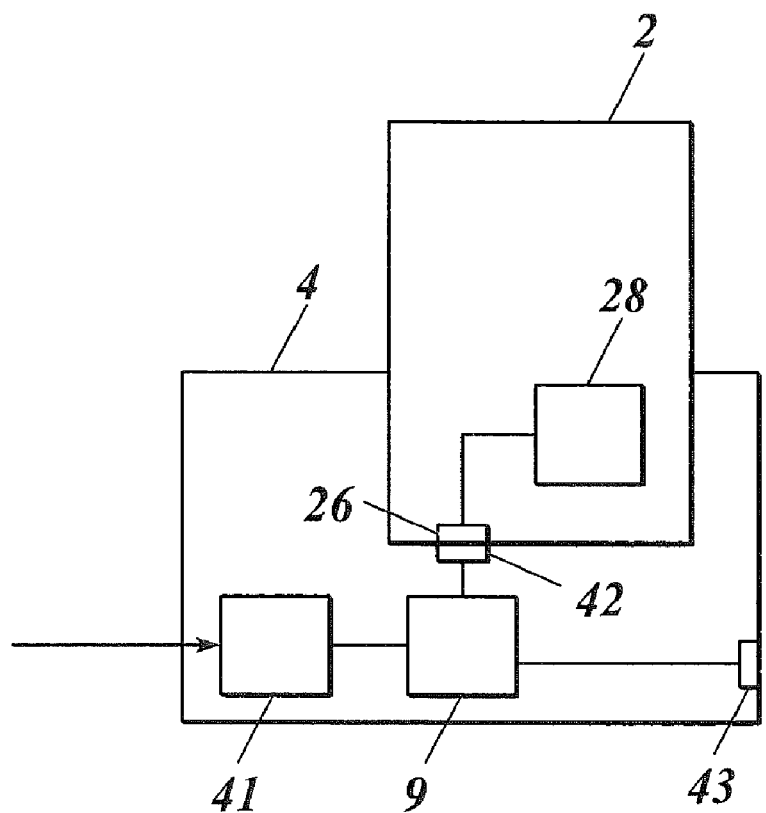
FIG. 10 is an explanatory diagram showing the connecting state of the radiation image detecting apparatus shown in FIG. 9 to the cradle.

FIG. 10 is a view schematically showing the state in which the radiation image detecting apparatus 2 is mounted on the cradle 4.

When the radiation image detecting apparatus 2 is mounted on the cradle 4, the connection of the cradle output connector section 42 to the detecting apparatus side connector section 26 is detected by the connection detecting section 90. The detection result by the connection detecting section 90 is output to the charging current setting section 91 of the charge controlling circuit 9 provided in the cradle 4.

When the detection result is transmitted from the connection detecting section 90 to the charging current setting section 91, the charging current setting section 91 sets the value of the charging current to large, for example, 2 amperes, in order to charge the battery 28 with the large current according to the detection result. The set result by the charging current setting section 91 is output to the switch control section 92. The detection result of the voltage of the battery 28 is output from the battery voltage detecting section 96 to the switch control section 92. The value of the charging current flowing into the battery 28 is output from the charging current detecting section 95 to the switch control section 92. The switch control section 92 judges whether it is needed or not to charge the battery 28 on the basis of the results output from these battery voltage detecting section 96 and charging current detecting section 95. When the switch control section 92 judges that the charging is needed, the switch control section 92 controls the charging switch 93 in order to perform the charging with the current value (for example 2 amperes) set by the charging current setting section 91. Thereby, a constant current charging of the current value of 2 amperes is started.

During the charging, detection results are output from the battery voltage detecting section 96 and the charging current detecting section 95 to the switch control section 92 as needed, and the switch control section 92 always judges which of the constant current charging and the constant voltage charging should be performed and whether the charging should be continued or ended on the basis of the detection results. Then, when the voltage of the battery 28 output from the battery voltage detecting section 96 reaches a predetermined value or more, the switch control section 92 controls the charging switch 93 in order to switch from the constant current charging to the constant voltage charging.

Moreover, when the current value output from the charging current detecting section 95 reaches a predetermined value or less, the switch control section 92 judges that the charging should be ended, and controls the charging switch 63 to be switched off. Thereby, the charging of the battery 28 ends.

Figure 11:
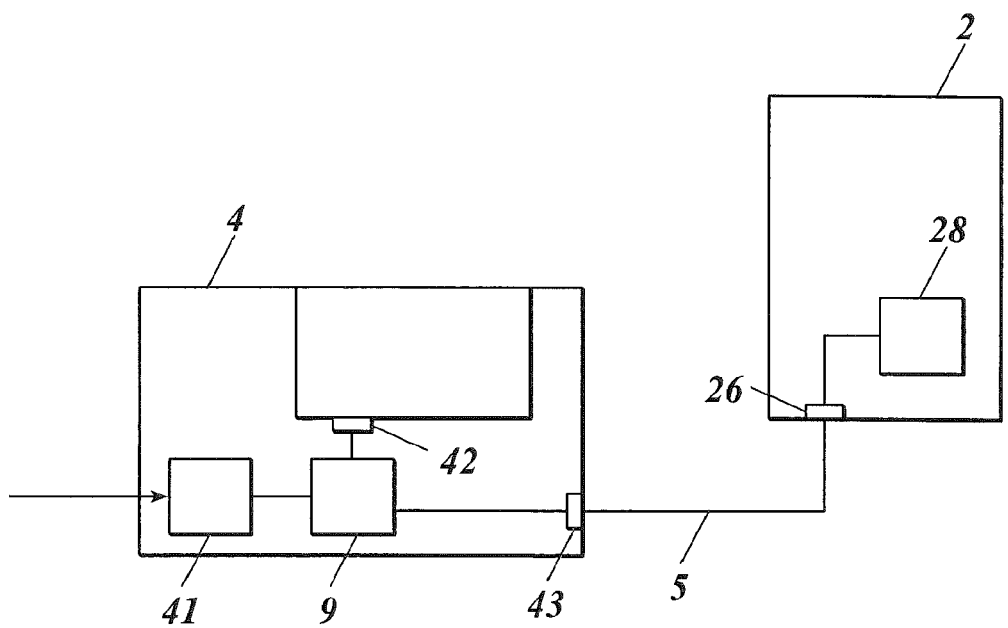
FIG. 11 is an explanatory diagram showing the connecting state of the radiation image detecting apparatus shown in FIG. 9 to the cable.

Next, FIG. 11 is a view schematically showing the state in which the cable 5 is connected to the radiation image detecting apparatus 2.

When the cable 5 connected to the cable-use output connector section 43 of the cradle 4 is connected to the detecting apparatus side connector section 26 of the radiation image detecting apparatus 2, the connection is detected by the connection detecting section 90. The detection result by the connection detecting section 90 is output to the charging current setting section 91 of the charge controlling circuit 9.

When the detection result is transmitted from the connection detecting section 90 to the charging current setting section 91, the charging current setting section 91 sets the value of the charging current to small, such as 0.1 amperes, in order to charge the battery 28 with the small current according to the detection result. The set result by the charging current setting section 91 is output to the switch control section 92. The detection result of the voltage of the battery 28 is output from the battery voltage detection section 96 to the switch control section 92, and the value of the charging current flowing into the battery 28 is output from the charging current detecting section 95 to the switch control section 92. The switch control section 92 judges whether the charging of the battery 28 is needed or not on the basis of these results output from the battery voltage detecting section 96 and the charging current detecting section 95. When the switch control section 92 judges that the charging is needed, the switch control section 92 controls the charging switch 93 in order to perform the charging with the current value (for example, 0.1 amperes) set by the charging current setting section 91. Thereby, the constant current charging with the current value of 0.1 amperes is started.

Moreover, in this case, radiography, data processing, and the like can be performed while charging of the battery 28 is performed, and that electric power is supplied from the battery 28 or an external power source through the detecting apparatus side connector section 26 to each of the function sections of the radiation image detecting apparatus 2. Incidentally, when radiography and the like are being performed while charging, the current value to be supplied becomes larger since the power is supplied to each of the function sections at the same time.

During charging, the detection results are output from the battery voltage detecting section 96 and the charging current detecting section 95 to the switch control section 92 as needed, and the switch control section 92 always judges which of the constant current charging and the constant voltage charging should be performed and whether the charging should be continued or ended on the basis of the detection results. Then, when the voltage of the battery 28 output from the battery voltage detecting section 96 becomes the predetermined value or more, the switch control section 92 controls the charging switch 93 in order to switch the constant current charging to the constant voltage charging.

Moreover, when the current value output from the charging current detecting section 95 becomes the predetermined value or less, the switch control section 92 judges that the charging should be ended and controls the charging switch 93 to be switched off. Thereby, the charging of the battery 28 ends.

As described above, according to the present embodiment, when the cradle output connector section 42 is connected to the detecting apparatus side connector section 26, high-speed charging can be performed with a large current. When the cable 5 is connected to the detecting apparatus side connector section 26, the processing of radiography and the like can be performed while charging with a small current.

When the cable 5 is connected to the detecting apparatus side connector section 26, the current-carrying capacity of the cable 5 can be made to be small in order to reduce the charging current, and the cable 5 can be thinner. Thereby, the property to pull the radiation image detecting apparatus 2 around is improved, and radiography and the like can easily be performed without being anxious about the residual quantity of the battery 28 while the charging of the battery 28 is being performed.

Moreover, because the current flowing through the cable 5 is made to be small, the power loss for the voltage drop owing to the cable 5 can be reduced.

Moreover, when the cable 5 is connected to the detecting apparatus side connector section 26, charging is performed with a small current. Thereby the quantity of noise generated from the charge controlling circuit 9 is suppressed. Consequently, the influences of the image quality owing to charging can be suppressed.

Moreover, in the present embodiment, the charge controlling circuit 9 is provided in the cradle 4 in place of being provided in the radiation image detecting apparatus 2, and consequently the radiation image detecting apparatus 2 is hardly influenced by the heat generated in the charge controlling circuit 9, thereby the deterioration of the image quality owing to the heat can be suppressed.

Moreover, when the cradle output connector section 42 is connected to the detecting apparatus side connector section 26, radiography performed in the connecting state is not possible. Consequently it is unnecessary to be anxious about the influences owing to the generation of noise by charging, and the like. Accordingly, in such a state, short time charging can be performed by charging with a large current, which is convenient.

Incidentally, in the present embodiment, the charge controlling circuit 9 is provided in the cradle 4 as an example. However, the charge controlling circuit 9 is not limited to be provided in the cradle 4.

For example, an external device, such as the wireless access point 113, in the radiographing room R1 (see FIG. 5) may receive electric power from an external power source and may be connected to the cradle 4 and the cable 5, and a charge controlling circuit may be provided in the external device to control charging and the like when the battery 28 is being charged.

It is needles to say that it is the same as the first embodiment that the present invention is not limited to the embodiment described above, but can suitably be changed.

INDUSTRIAL APPLICABILITY

The present invention can be used in the technical field in which medical image radiography is performed.

The invention claimed is:

1. A radiation image detecting system comprising:
   a cassette type radiation image detecting apparatus capable of being driven by electric power supplied from a built-in battery which supplies the electric power to each of function sections;
   a charge controlling circuit to control charging of the battery;
   a cradle supplying electric power from an outside to the radiation image detecting apparatus by placing the radiation image detecting apparatus thereon; and
   a cable capable of supplying electric power from the outside to the radiation image detecting apparatus by being connected to the radiation image detecting apparatus, wherein
   the radiation image detecting apparatus includes a connection section being electrically connected to each of the cradle and the cable to receive the electric power;
   the battery is charged by the cradle being connected to the connection section and by the cable being connected to the connection section; and
   the charge controlling circuit switches a charging current between a time when the cradle is connected to the connection section and a time when the cable is connected to the connection section.

2. The radiation image detecting system according to claim 1, wherein the charge controlling circuit is provided inside the cradle.

3. The radiation image detecting system according to claim 1, further comprising:
   detection section for detecting which of the cradle and the cable is connected to the connection section, wherein
   the charge controlling circuit switches the charging current according to a detection result of the detection section.

4. The radiation image detecting system according to claim 1, wherein
   the radiation image detecting apparatus can select a driven state from two driven states of a battery-driven state in which the radiation image detecting apparatus is driven by obtaining the electric power from the battery and an external feeding-driven state in which the radiation image detecting apparatus is driven by receiving the electric power supplied from the outside through the cradle or the cable, and
   the battery is charged in the external feeding-driven state.

5. The radiation image detecting system according to claim 1, wherein
   the battery is a lithium ion capacitor.

* * * * *